(12) United States Patent
Walsh et al.

(10) Patent No.: US 6,237,105 B1
(45) Date of Patent: May 22, 2001

(54) SIGNAL PROCESSOR WITH INTELLIGENT FEEDBACK TO ENSURE FUNCTIONALITY OF MICROPROCESSOR AND STATE MACHINE BASED PROGRAMMABLE PULSE GENERATORS IN THE PRESENCE OF CLOCK AND POWER SUPPLY DISTURBANCES

(75) Inventors: Kevin K. Walsh, Glendale; Roman Korsunsky, Scottsdale, both of AZ (US); James D. Reinke, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 08/054,496

(22) Filed: Apr. 26, 1993

(51) Int. Cl.⁷ ........................................... G06F 1/04

(52) U.S. Cl. ........................................ 713/500; 713/601

(58) Field of Search .................... 395/550, 307, 395/269; 307/265, 267; 370/58; 235/153 AC; 713/400, 401, 500, 600

(56) References Cited

U.S. PATENT DOCUMENTS

| 4,025,768 | * | 5/1977 | Missioy et al. | 235/153 AC |
|---|---|---|---|---|
| 4,635,249 | * | 1/1987 | Bortolini et al. | 370/58 |
| 4,636,656 | * | 1/1987 | Snowden et al. | 307/267 |
| 4,745,629 | * | 5/1988 | Essig et al. | 377/20 |
| 4,959,557 | * | 9/1990 | Miller | 307/265 |
| 5,227,672 | * | 7/1993 | Sawtell | 307/269 |

* cited by examiner

Primary Examiner—Majid A. Banankhah
(74) Attorney, Agent, or Firm—Reed A. Duthler; Harold R. Patton (57) ABSTRACT

A signal processor operates on a microprocessor or state machine based system to ensure that the central processing unit (CPU) and pulse generator (PG) have finished their instructions before allowing a new transition on the system master clock. The CPU and PG contain circuitry which allows them to indicate when they are busy. These signals are fed to the signal processor to indicate when the CPU and PG are ready to start another instruction. The signal processor functions to prevent a noise glitch on the system clock from causing another operation to start before the one in process has finished. The output of the signal processor becomes the master clock signal used by the system.

8 Claims, 13 Drawing Sheets

SIGNAL PROCESSOR WITH INTELLIGENT FEEDBACK TO ENSURE FUNCTIONALITY OF MICROPROCESSOR AND STATE MACHINE BASED PROGRAMMABLE PULSE GENERATORS IN THE PRESENCE OF CLOCK AND POWER SUPPLY DISTURBANCES

BACKGROUND OF THE INVENTION

1. Field of the Invention

The present invention generally relates to implantable medical devices and more specifically relates to a system and method for monitoring master clock oscillator operation in microprocessor and state machine based implantable pulse generators and for modifying the master clock oscillator output signal in response to a low power intelligent feedback signal from the monitoring system.

2. Description of the Prior Art

Early pulse generators such as cardiac pacemakers were asynchronous in operation, providing stimulating pulses to the heart at a fixed rate independent of the physiologic demand of the patient. In recent years, pacemakers which vary the pacing rate in response to numerous patient parameters have become widely available. For example, a rate responsive pacemaker may be responsive to patient physical activity. Such a pacemaker includes a sensor which produces an output that varies between a maximum sensor output level and a minimum sensor output level and provides for a pacing rate which typically varies between a selectable lower pacing rate and an upper pacing rate. Such a pacemaker which utilizes a piezoelectric transducer, is disclosed in U.S. Pat. No. 4,485,813, issued to Anderson et al., and assigned to Medtronic, Inc.

It has become common practice in recent years to provide programmable pacemakers in order to permit the physician to select and adjust the desired parameters to match or optimize the pacing system to the heart patient's physiologic requirements in an effort to minimize patient problems and to prolong or extend the useful life of an implanted pacemaker. Such pacemakers typically are microprocessor based systems or are based on state machines requiring accurate clocking, or timing signals. These timing signals are used to synchronize the various electronic functions within the pacemaker. Generally, a single master clock source, such as a clock oscillator, is employed to provide a periodic clocking signal at a single frequency. This clocking signal can be divided by various numerical values to result in a plurality of separate clock signals, all of which are at a fraction of the master clock signal for coordinating various handshaking operations within the programmable pacemaker.

Accurate clock signals are essential for proper functioning of the programmable pacemaker. If the frequency of the master clock signal deviates from its predetermined clock frequency, the pacemaker will not perform in the manner as intended. For example, the master clock circuit, typically including a piezo-electric crystal, may be susceptible to a noisy environment in certain rare circumstances including EMI and Cautery, and as a result not be able to guarantee the master clock signal that is delivered to the programmable pacemaker system meets the clock duty cycle requirements. In these rare cases, if the master clock signal is too narrow either in the positive or the negative half of the signal, the microprocessor, telemetry port and programmable pacemaker itself may fail to function properly. Thus, a failure at any time will result in operational failure where any programmable pacemaker block is state machine based.

SUMMARY OF THE INVENTION

To avoid operational failures attributable to an out-of-spec implantable pulse generator master clock, a new sub-system block is added. This block receives the output clock signal from the master clock, and from it, generates a modified master clock signal that replaces the original master clock signal to control the handshaking operations within the pulse generator to ensure proper operation. The function of the new sub-system block is to guarantee that the modified master clock signal delivered to the rest of the pulse generator system always has a duty cycle sufficient to ensure correct functionality of the system microprocessor, the programmable pulse generator itself and the telemetry port.

The microprocessor, pulse generator and telemetry port all require master clock signals received to be of certain duration. The pulse generator and system microprocessor generate event completion signals during each master clock period. These event completion signals allow the pulse generator and system microprocessor to perform one asynchronous event after another which are not synchronized with the master clock. The event completion signals are used to trigger the start of the subsequent, but in either case, never the last event. The inventive sub-system block guarantees a sufficient duty cycle by using the event completion signals from the pulse generator and system microprocessor. The sufficiency is achieved by incorporating an appropriate time delay into the modified master clock signal which is slightly longer than the last event in each half of the modified master clock signal. Thus, the combination of the event completion signals from the microprocessor and the pulse generator, combined with the delay provided by the inventive sub-system, provide the missing event completion signal for each half of the master clock cycle. The new half cycle event completion signals are then used to guarantee the duty cycle of the original master clock, thereby ensuring uninterrupted functionality of the implantable pulse generator, even during external disturbances of the battery voltage or other conditions which create disturbances of the master clock period or duty cycle.

Another feature of the inventive sub-block is the elimination of any necessity for a back-up master clock for redundancy. The sub-block design requires only 100–150 nanoamperes of current for full functionality, allowing it to operate simultaneously along with the original master clock within the implantable pulse generator system. The new sub-block does not require that it be left in a standby mode for conservation of energy.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENT

Figure 1A:
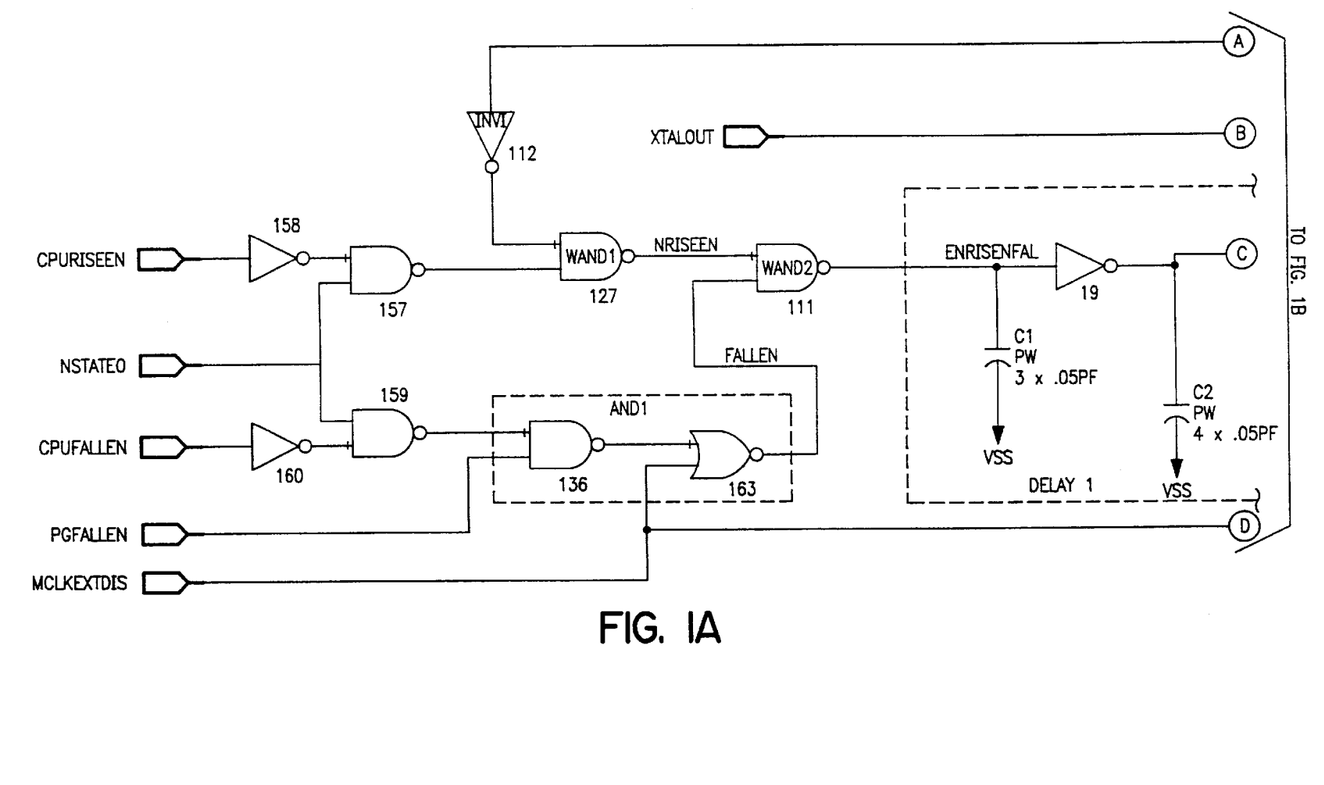
FIG. 1A is a detailed circuit diagram illustrating a front end portion of a preferred embodiment of the inventive sub-system for modifying a master clock signal to control timing relationships within an implantable pulse generator.
Figure 1B:
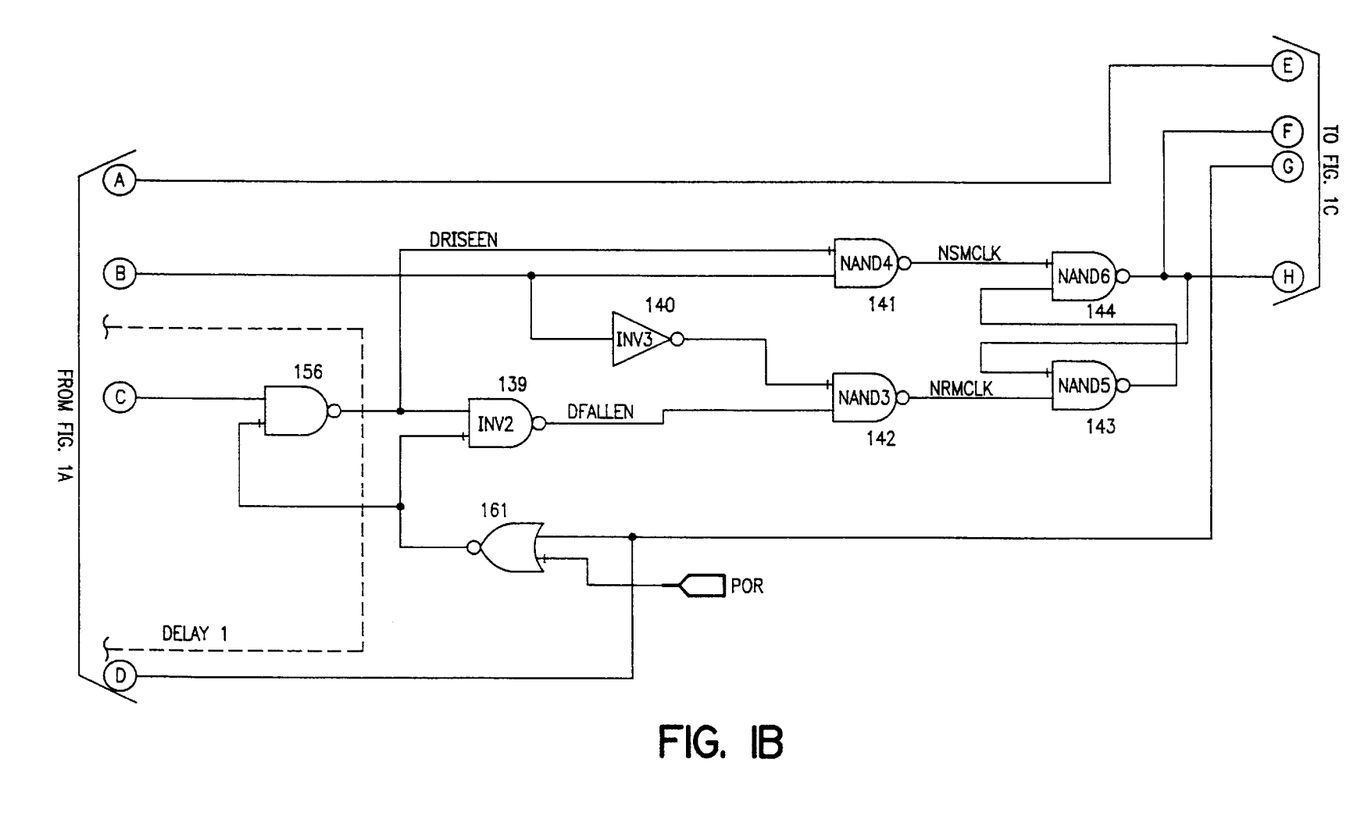
FIG. 1B is a detailed circuit diagram illustrating a middle portion of a preferred embodiment of the inventive sub-system for modifying a master clock signal to control timing relationships within an implantable pulse generator.
Figure 1C:
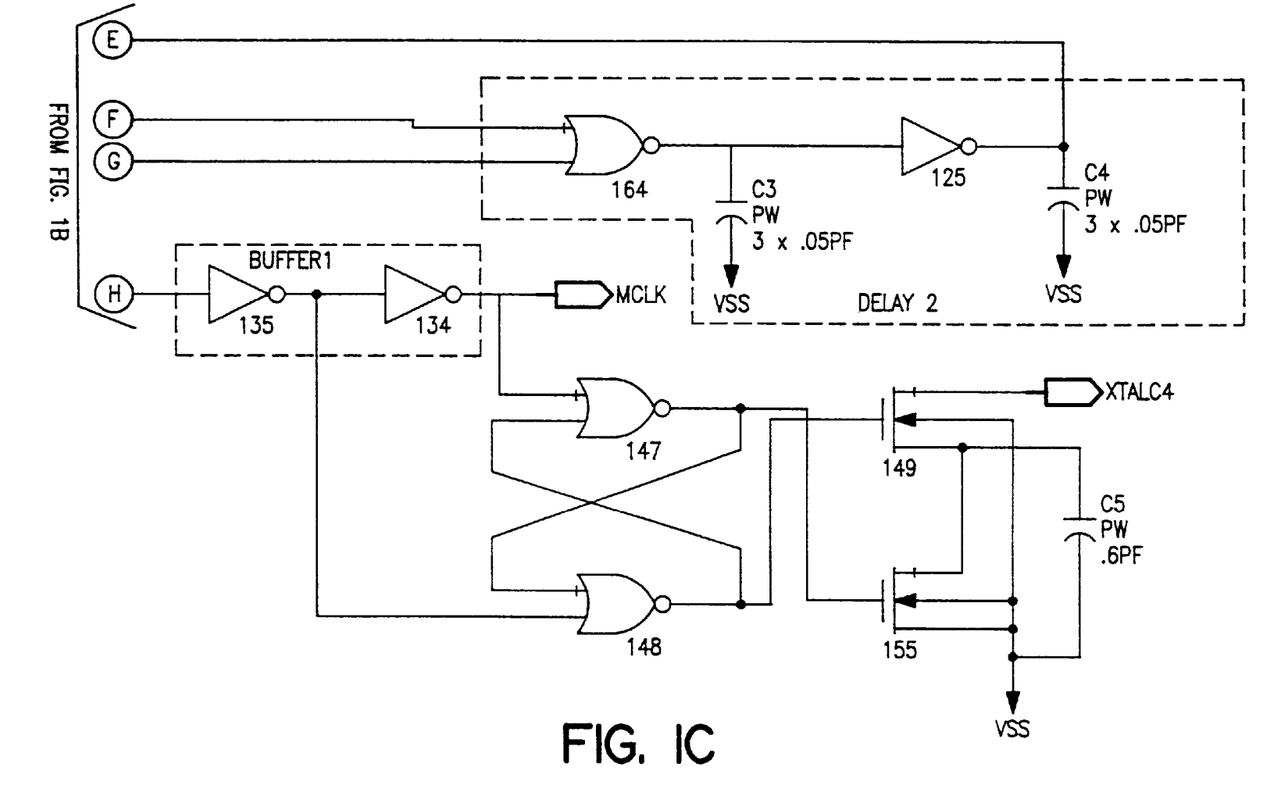
FIG. 1C is a detailed circuit diagram illustrating a back end portion of a preferred embodiment of the inventive sub-system for modifying a master clock signal to control timing relationships within an implantable pulse generator.
Figure 2:
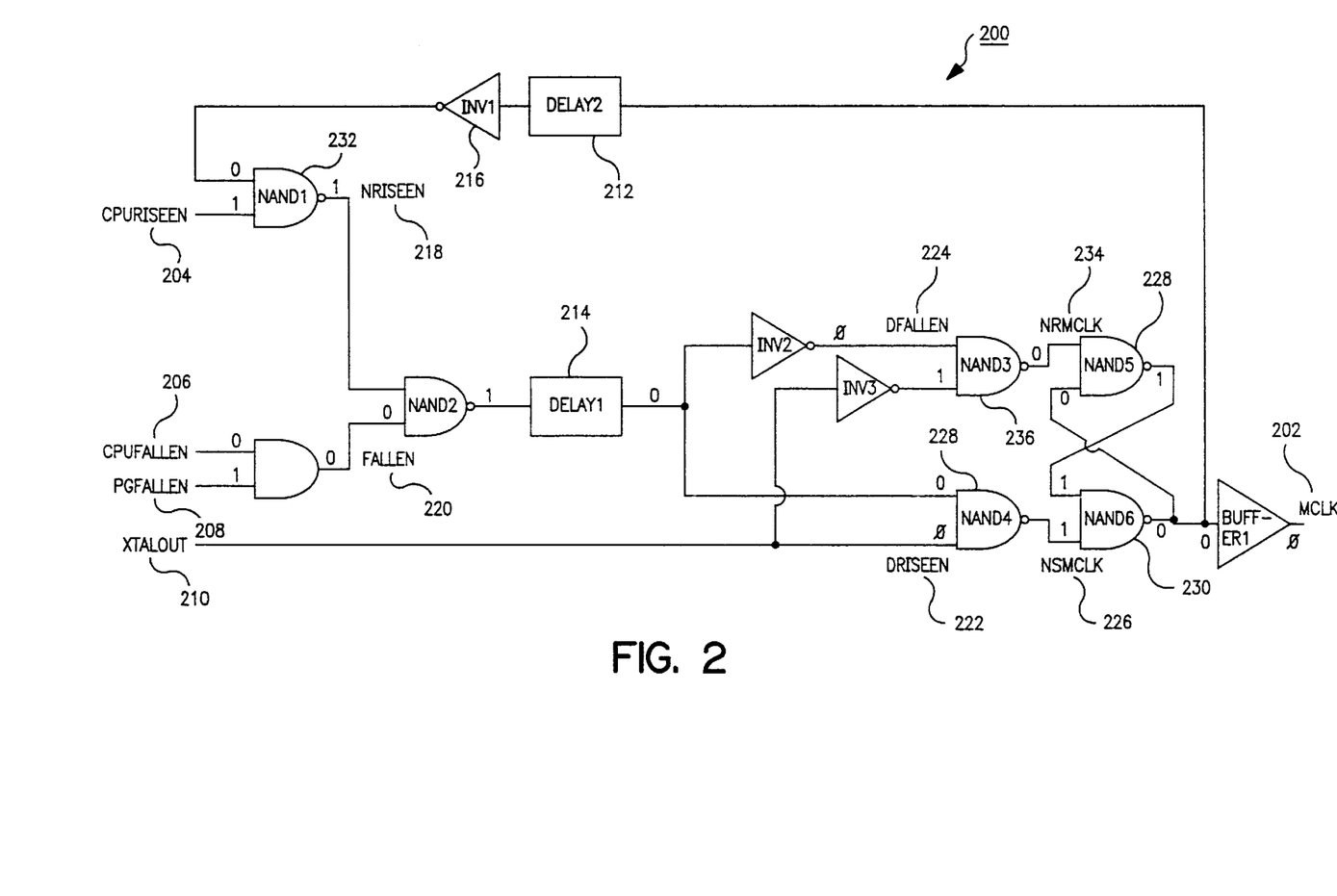
FIG. 2 is a simplified schematic diagram of the detailed circuit illustrated in FIGS. 1A, 1B and 1C.

A presently preferred embodiment of the invention is illustrated in FIGS. 1A, 1B, 1C and 2. FIGS. 3 through 11 have been included to illustrate how the preferred embodiment functions. FIG. 2 will be used to describe the preferred embodiment hereinafter since it is a simplified version of FIGS. 1A, 1B and 1C; and because many of the system components depicted in FIGS. 1A, 1B and 1C are either not critical or are peripheral to the functionality of the inventive system.

Moving now to FIG. 2, a simplified schematic diagram of the preferred embodiment for the inventive sub-system 200 is illustrated. The purpose of the sub-system 200 depicted in FIG. 2, as discussed hereinbefore, is to lock out all transitions on the modified master clock signal MCLK 202 until the pacing system central processing unit (CPU) and pulse generator (PG) have finished their instructions. The CPU starts operations on both rising and falling edges of MCLK 202, and the PG starts its operations on the rising edge of MCLK 202. Simply stated, the function of the preferred embodiment of the inventive sub-system 200 depicted in FIG. 2 is to prevent a noise glitch on the master clock signal from causing another operation to start before the one in process has finished. The CPU and PG contain circuitry which allows them to generate signals 204, 206 and 208 indicating when they are busy. These signals 204, 206 and 208 are fed to the inventive sub-system 200 input circuitry to indicate when the CPU and PG are ready to start another instruction. As stated hereinbefore, the output of the inventive sub-system 200 is the modified master clock signal MCLK 202 used by the pacing or implantable pulse generator system.

The XTALOUT 210 signal input to sub-system 200 is the output of a crystal oscillator familiar to those of ordinary skill in the art of implantable pulse generators. XTALOUT 210 is the master clock signal used to set the base clock period for the modified master clock MCLK 202 signal. Thus, when the sub-system 200 is operating in its normal mode of operation, the MCLK 202 output signal is equivalent to the master clock XTALOUT 210 input signal. The CPURISEEN 204 signal is a signal coming from the implantable pulse generator CPU which is normally high except while the CPU is in the process of performing an instruction which is started on the falling edge of MCLK 202. While the CPU is executing an instruction started on the falling edge of MCLK 202, the CPURISEEN 204 signal is held low until the instruction is finished at which time CPURISEEN 204 returns high indicating that the CPU can allow a rising edge to occur on MCLK 202.

The CPUFALLEN 206 signal comes from the implantable pulse generator CPU and indicates when the CPU is in the process of performing an instruction started off the rising edge of MCLK 202. This signal 206 is normally high, but is low during the period of time that the CPU is executing an instruction started off the rising edge of MCLK 202. CPUFALLEN 202 transitions high when the instruction is completed indicated that the CPU can allow a falling edge to occur on MCLK 202.

The PGFALLEN signal comes from the PG or pulse generator circuitry and indicates when the PG is processing data. The PG starts the processing at the rising edge of MCLK 202, and holds PGFALLEN low while it is processing the data. PGFALLEN transitions high when the PG event is finished indicating that the PG can allow a falling edge to occur on MCLK 202.

Figure 3:
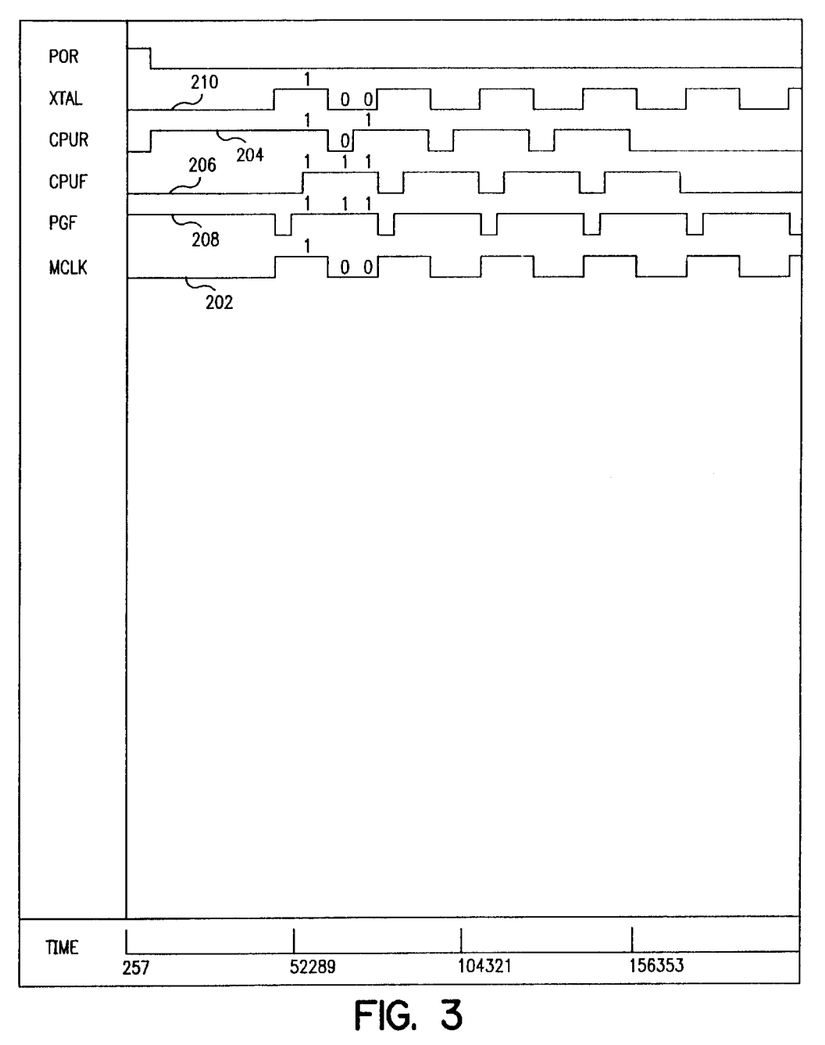
FIG. 3 is a simulation plot illustrating normal device operation for a programmable implantable pulse generator; the master clock signal duty cycle is normal and the modified master clock signal follows the original master clock signal.

It can be seen that FIG. 3 contains an element DELAY2 212. Functionally, DELAY2 212 is used to insure that MCLK 202 has been in its last state for at least DELAY2 time before allowing a transition on XTALOUT 210 to feed through to MCLK 202. This delay time is used to insure that the CPU or PG has a chance to start its operation and indicate that the aforementioned operation has started before MCLK 202 is allowed to make a transition. A second element DELAY1 214 is used to provide an additional delay between the time the rise and fall enable signals 204, 206 and 208 from the CPU and PG occur to indicate they are ready for the next clock transition, and the signals allowing the clock transition to occur. In the event that neither the PG or the CPU is executing instructions, the total delay before the sub-system 200 is armed for the next clock transition is the sum of DELAY1 214 and DELAY2 212. This feature provides some clock frequency limiting for other implantable pulse generator circuits which operate much faster than the CPU or PG, but still require some delay to finish their operations.

With continued reference to FIG. 2, and keeping in mind the operating boundaries of the preferred embodiment hereinbefore discussed, operation of the inventive sub-system can now be more readily appreciated by describing how the embodiment of FIG. 2 functions with reference to FIGS. 3, 4, 5 and 6 in describing four different exemplary operating modes.

In the first, or normal mode of operation, illustrated in FIG. 3, the MCLK 202 output of sub-system 200 is equivalent to the XTALOUT 210 signal coming into sub-system 200. In this mode of operation, CPURISEEN 204, CPUFALLEN 206 and PGFALLEN 208 will all be high indicating that they are ready to start an operation. For the case where XTALOUT 210 is low, MCLK 202 is low, the output of INV1 216 is high and NRISEEN 218 is low. The signals FALLEN 220 and delayed RISEEN (DRISEEN) 222 are both high, but delayed FALLEN (DFALLEN) 224 is low. These conditions indicate that sub-system 200 is now armed and ready for a transition from low to high on XTALOUT 210. When XTALOUT 210 makes the transition from low to high, the output NSMCLK 226 of NAND4 228 goes low and forces the output of the not-set not-reset NAND latch formed by NAND5 228 and NAND6 230 to go high and the buffered MCLK 202 output to transition from low to high. The output of the NAND latch feeds back to the input of NAND1 232 after a short delay (DELAY2) 212 forcing the NRISEEN 218 output of NAND1 232 high. As soon as both CPUFALLEN 206 and PGFALLEN 208 have gone high, FALLEN 220 goes high and after a short delay (DELAY1) 214, DFALLEN 224 will go high and DRISEEN 222 will go low. This activity then arms the sub-system 200 for a falling edge on XTALOUT 210 and locks out rising edges. When XTALOUT 210 makes the transition from high to low, the NRMCLK 234 output of NAND3 236 goes low causing the NAND latch to be reset and MCLK 202 to go low. This signal then feeds back to NAND1 232 through DELAY2 212 allowing NRISEEN 218 to go low as soon as CPURISEEN 204 goes high. After a period of DELAY1 214 subsequent to CPURISEEN 204 going high, DRISEEN 222 goes high and DFALLEN 224 goes low arming embodiment 200 for a rising edge from MCLK 202. FIG. 3 illustrates the timing relationships between CPURISEEN 204, CPUFALLEN 206, PGFALLEN 208, XTALOUT 210 and MCLK 202 during the normal mode of operation for the preferred embodiment 200 of the inventive sub-system.

Figure 4:
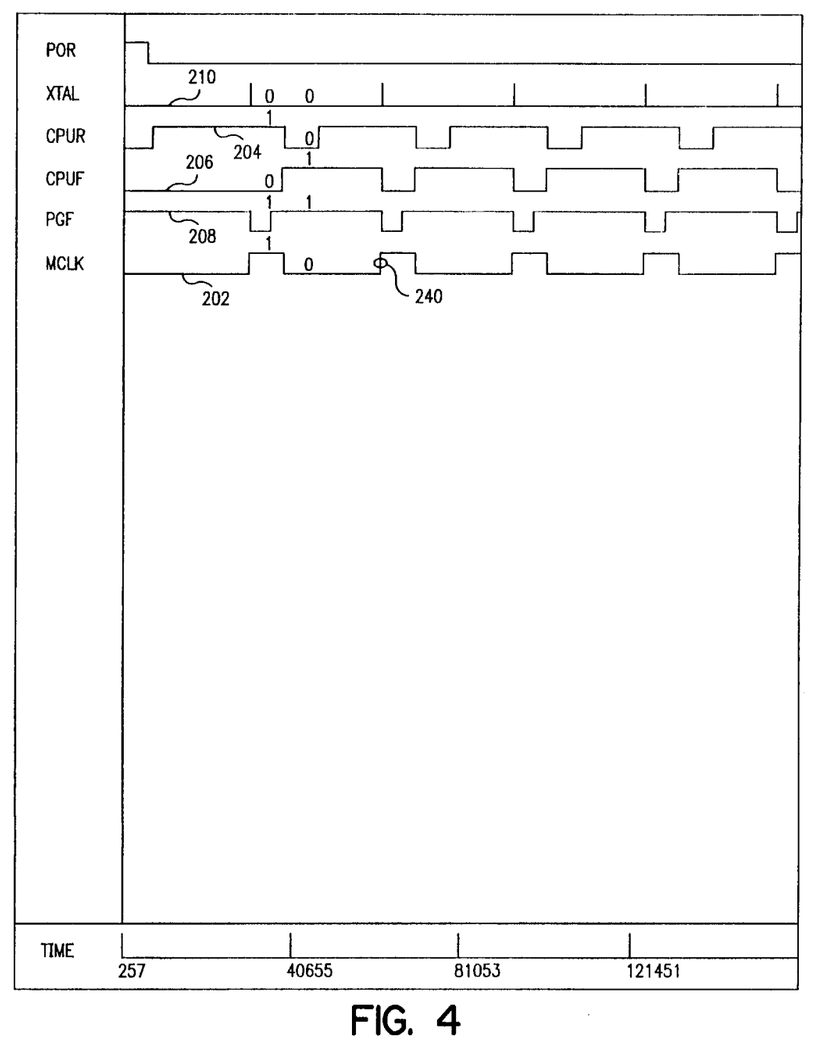
FIG. 4 is a simulation plot illustrating a device having a positive noise glitch of 250 ns which is insufficient for the microprocessor to complete its operation in the first half of a normal master clock cycle; and therefore the master clock signal is extended until the final operation in the first half master clock cycle is completed.

A second example of sub-system 200 operation is depicted in FIG. 4 which illustrates a timing diagram for a low duty cycle clock operation. In this case, XTALOUT 210 has a very low duty cycle, which forces sub-system 200 to increase the width of MCLK 202 beyond that required by the system CPU or the PG. This mode of operation can best be understood if one assumes initially that XTALOUT 210 is low, MCLK 202 is low, CPURISEEN 204 is high, CPUFALLEN 206 is high and PGFALLEN 208 is high. This condition forces NRISEEN 218 low, DRISEEN 222 high, FALLEN 220 high and DFALLEN 224 low. In addition, both NRMCLK 234 and NSMCLK 226 inputs to the NAND latch are now high. Using these initial conditions as the starting point for our analysis, sub-system 200 is now ready for a positive transition on XTALOUT 210. It can be seen from FIG. 2 that as soon as XTALOUT rising edge occurs, the NSMCLK 226 line goes low causing the output of the latch to be set and MCLK 202 to go high. This transition 240 of MCLK 202 can be seen in FIG. 4. A quick transition back low on XTALOUT 210 has no effect on MCLK 202 because changes to NRMCLK 234 are blocked by DFALLEN 224 being low. The NRMCLK 234 input to the NAND latch will not make the transition low until DELAY2 212 time has passed, CPUFALLEN 206 has gone high, PGFALLEN 208 has gone high and DELAY1 214 time has passed. Further reference to FIG. 4 shows that MCLK 202 will then go low a short period of time after the CPU and PG have finished their operations.

Figure 5:
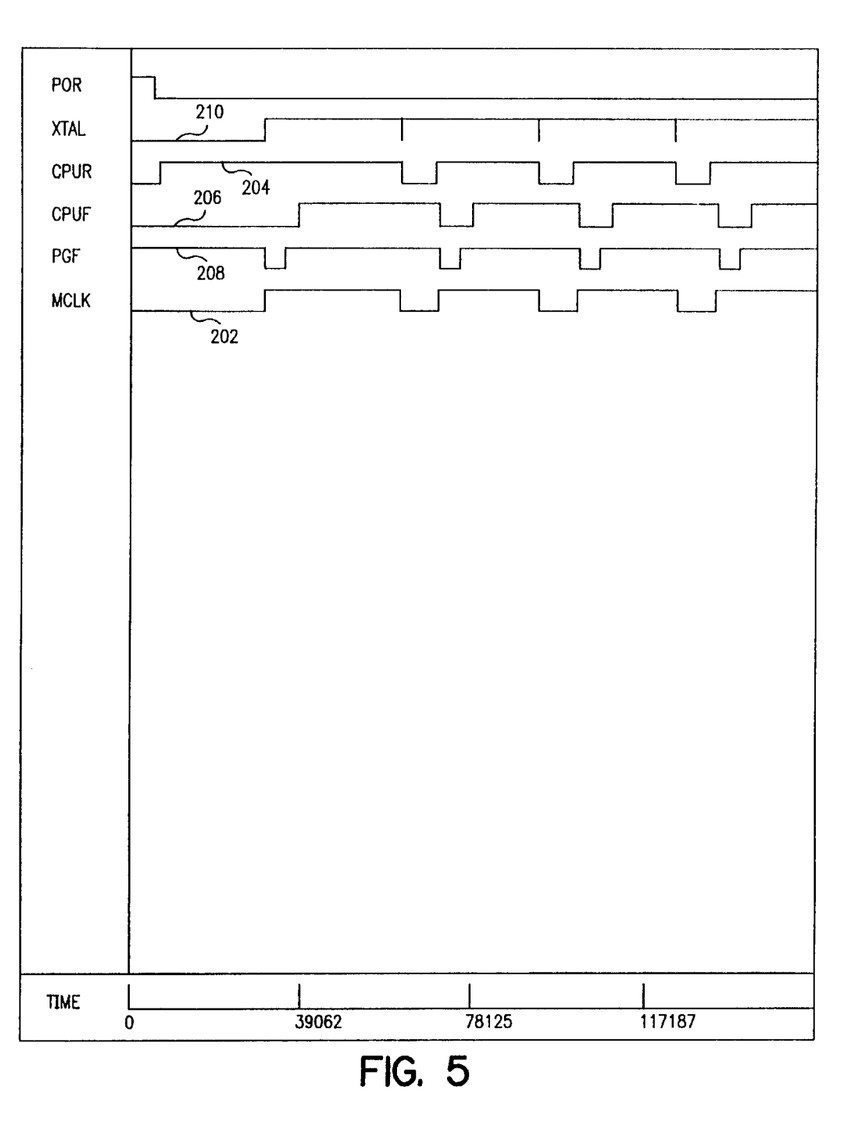
FIG. 5 is a simulation plot illustrating a device having a negative noise glitch of 250 ns which is insufficient for the microprocessor to complete its operation in the second half of a normal master clock cycle; and therefore the master clock signal is extended until the final operation in the first half master clock cycle is completed.

Still another mode of sub-system 200 operation occurs for the case where the XTALOUT 210 signal has a very high duty cycle. This mode of operation is illustrated in FIG. 5. In this case, sub-system 200 works to increase the width of the time low portion of the MCLK 202 signal to insure that the CPU has sufficient time to complete an operation started on the falling edge of MCLK 202.

Figure 6:
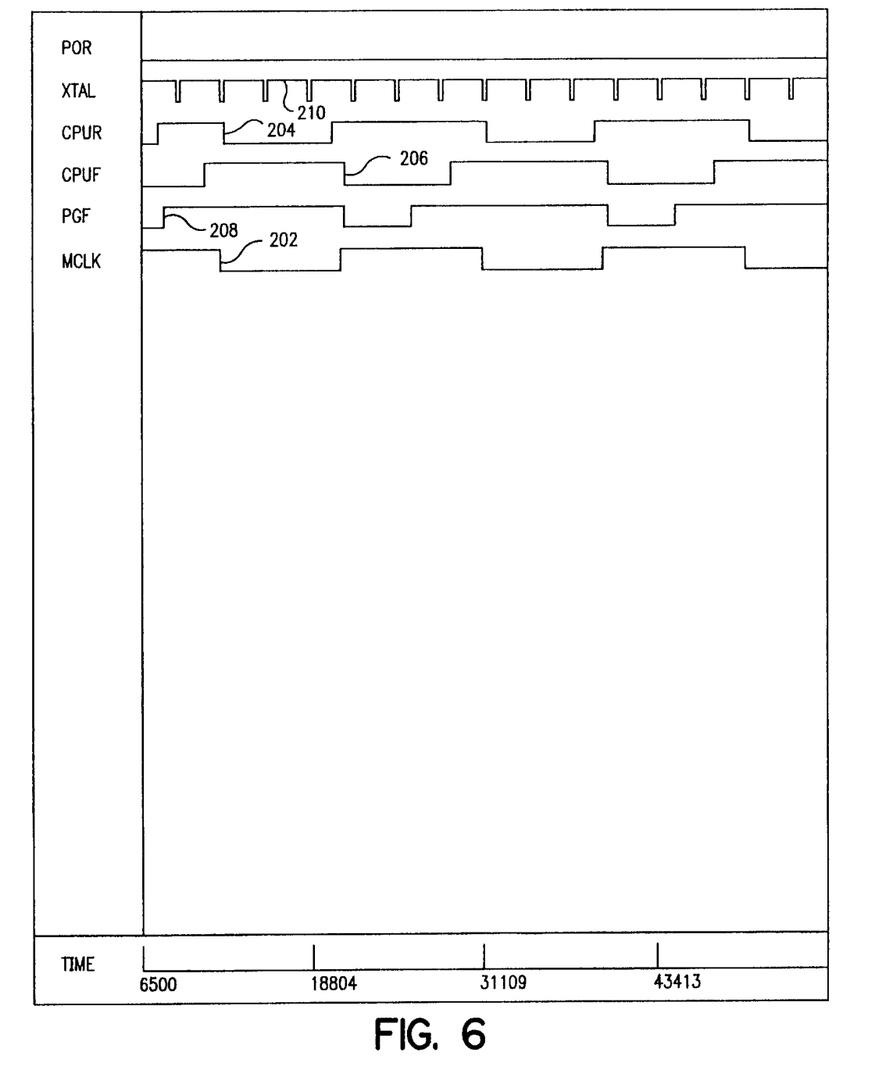
FIG. 6 is a simulation plot illustrating a device having a continuous high frequency noise present on the master clock signal; This is a situation in which the noise frequency is too high for the pulse generator or microprocessor to guarantee full functionality.

In the event that the XTALOUT 210 signal is running at a frequency much faster than the CPU and PG can operate, sub-system 200 (clock extension circuitry) will not permit the MCLK 202 to change until the CPU and/or PG have both finished their operations. FIG. 6 illustrates this mode of operation.

Figure 7:
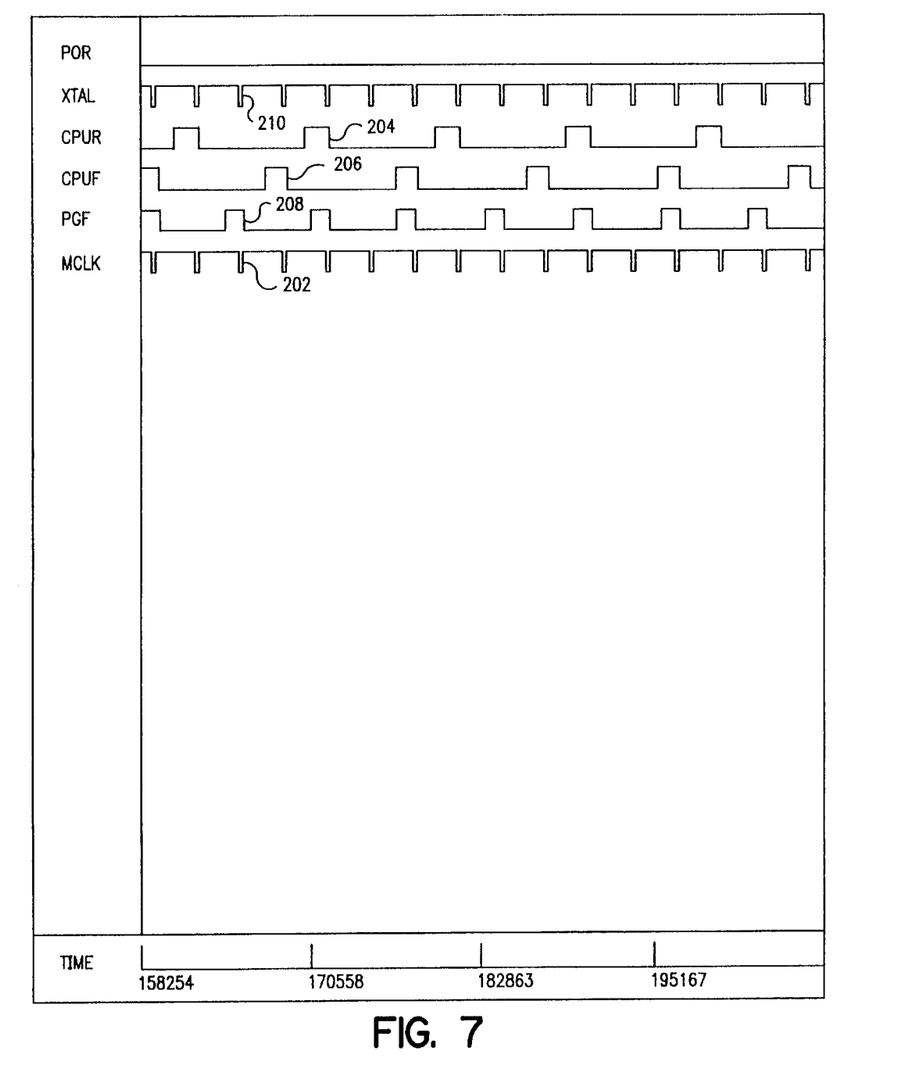
FIG. 7 is another simulation plot illustrating a device having a continuous high frequency noise present on the master clock signal; in this situation, the microprocessor is turned off to demonstrate that the modified master clock signal going to the other pulse generator functional blocks will be identical to the original master clock signal; this case reveals that the pulse generator will fail to operate properly.
Figure 8:
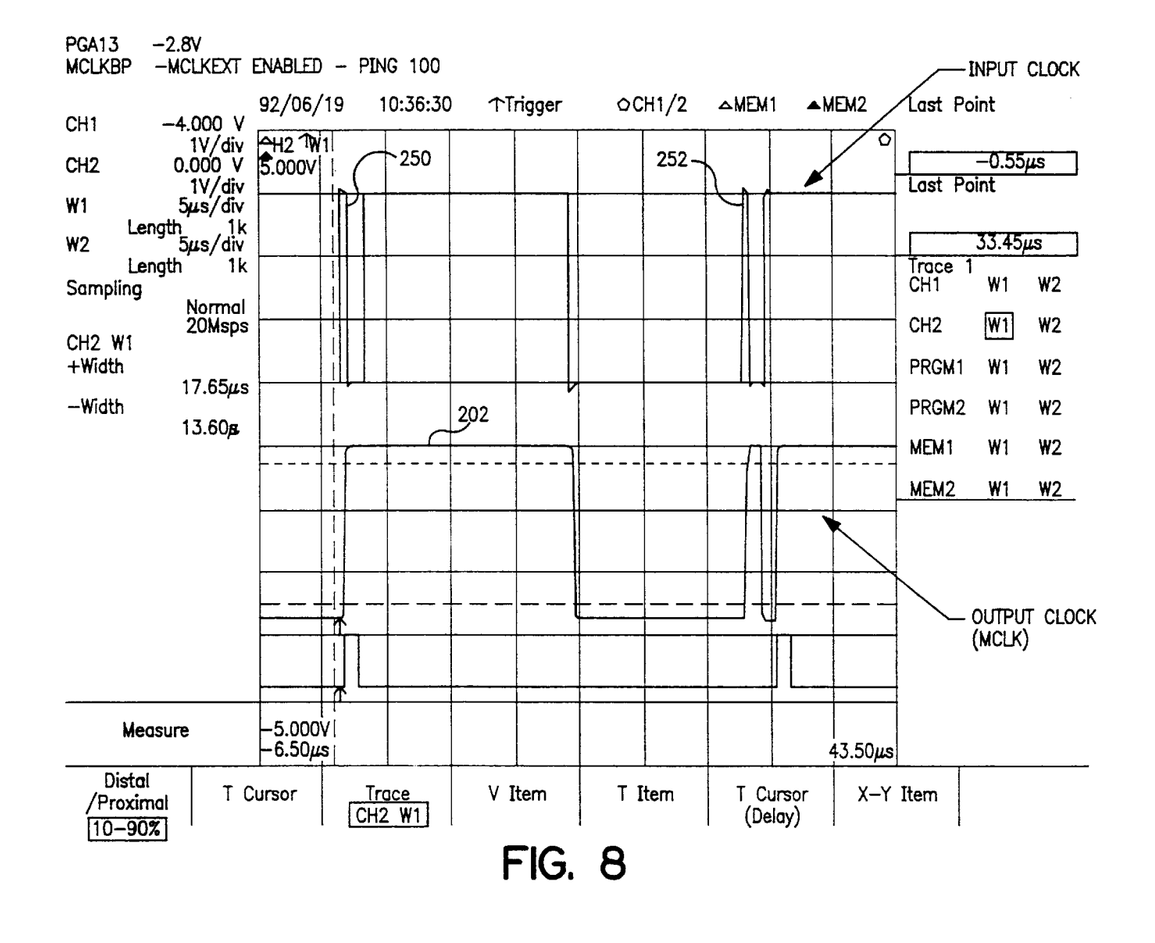
FIG. 8 is lab data from a functional device illustrating the master clock signal with a noise glitch superimposed on it; the modified master clock signal is going to the other pulse generator functional blocks; the first rising edge of the glitch is taken as the rising edge of the modified master clock signal because the device has completed all the required operations and was ready for the rising edge of the clock; the second glitch is shown propagating through to the modified master clock of the device because that clock cycle is sufficiently long to complete all of the necessary sequential events.

Moving on to FIG. 7, there is illustrated a condition where input clock XTALOUT 210 has a continuous high frequency noise present. This high frequency is too high for the implantable pulse generator or pacing system to operate properly. When sub-system 200 is turned on and functioning, it will not permit MCLK 202 to change until the CPU and/or PG have both finished their operations. This is the case depicted hereinbefore in FIG. 6. However, when sub-system 200 is turned off as depicted in FIG. 7, it is easily seen that the clock going to the implantable pulse generator will be identical to the incoming clock XTALOUT 210 with a continuous high frequency noise present. Thus, without sub-system 200 turned on, the pacing system or implantable pulse generator circuitry will fail to operate properly.

FIGS. 8, 9, 10 and 11 illustrate actual laboratory data from a functional device showing the effectiveness of the preferred embodiment of inventive sub-system 200 depicted in FIG. 2. Beginning with FIG. 8, there is illustrated operation of sub-system 200 with a noise glitch 250 superimposed on input clock XTALOUT 210. The output clock MCLK 202 is the main clock going to the implantable pulse generator or pacing system. It can be seen that the first rising edge of the glitch 250 is taken as the rising edge of MCLK 202. This is because the CPU and PG have completed all the required operations and were ready for the rising edge of MCLK 202. The second glitch 252 is shown propagating through to the modified master clock (sub-system 200) because that clock cycle is sufficiently long to complete all of the necessary sequential events.

Figure 9:
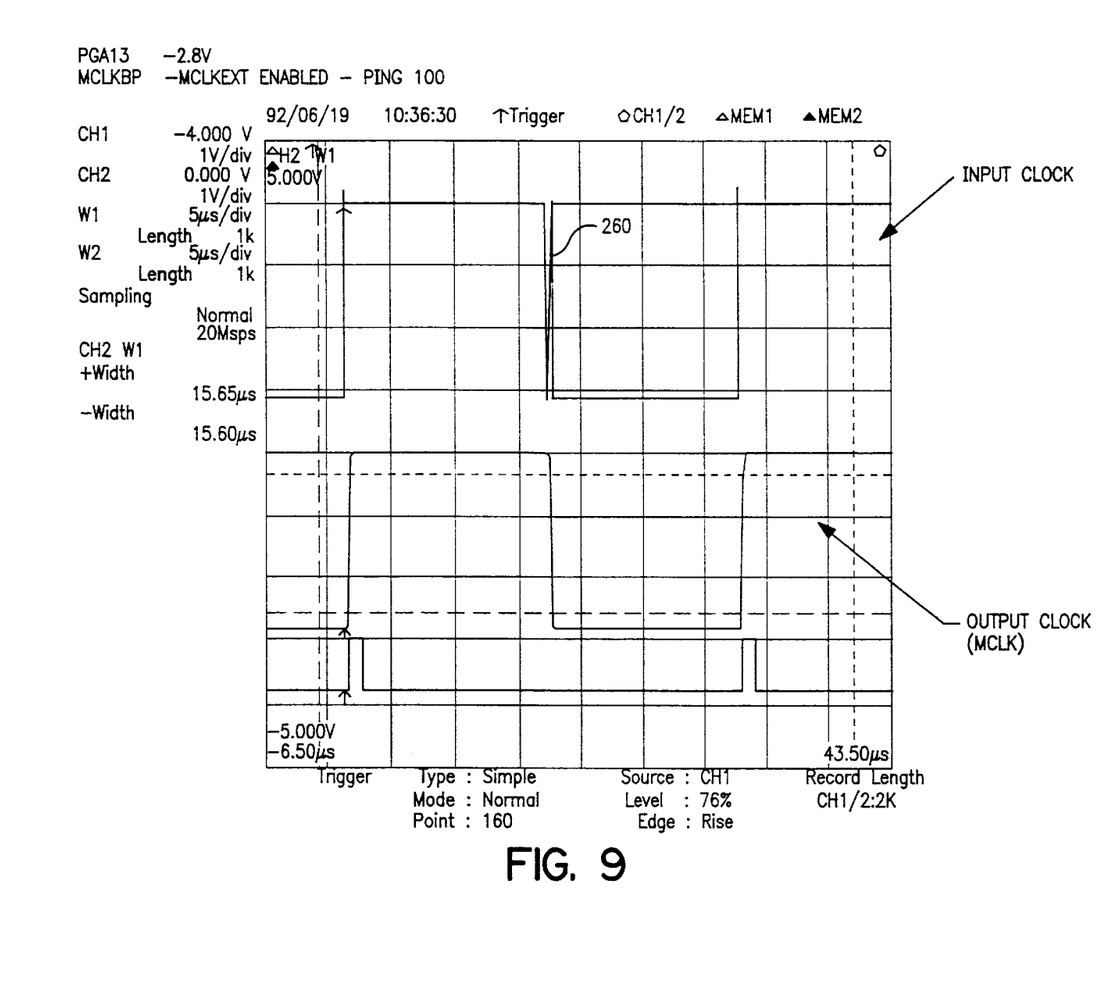
FIG. 9 is lab data from a functional device illustrating the inventive sub-block removing a glitch on the original master clock.

Moving now to FIG. 9, there is illustrated laboratory data from a functional device showing the effectiveness of the clock extender (sub-system 200) block in preventing a glitch 260 on input clock XTALOUT 210 from propagating through to output clock MCLK 202 which is ultimately delivered to the pacing system or implantable pulse generator.

Figure 10:
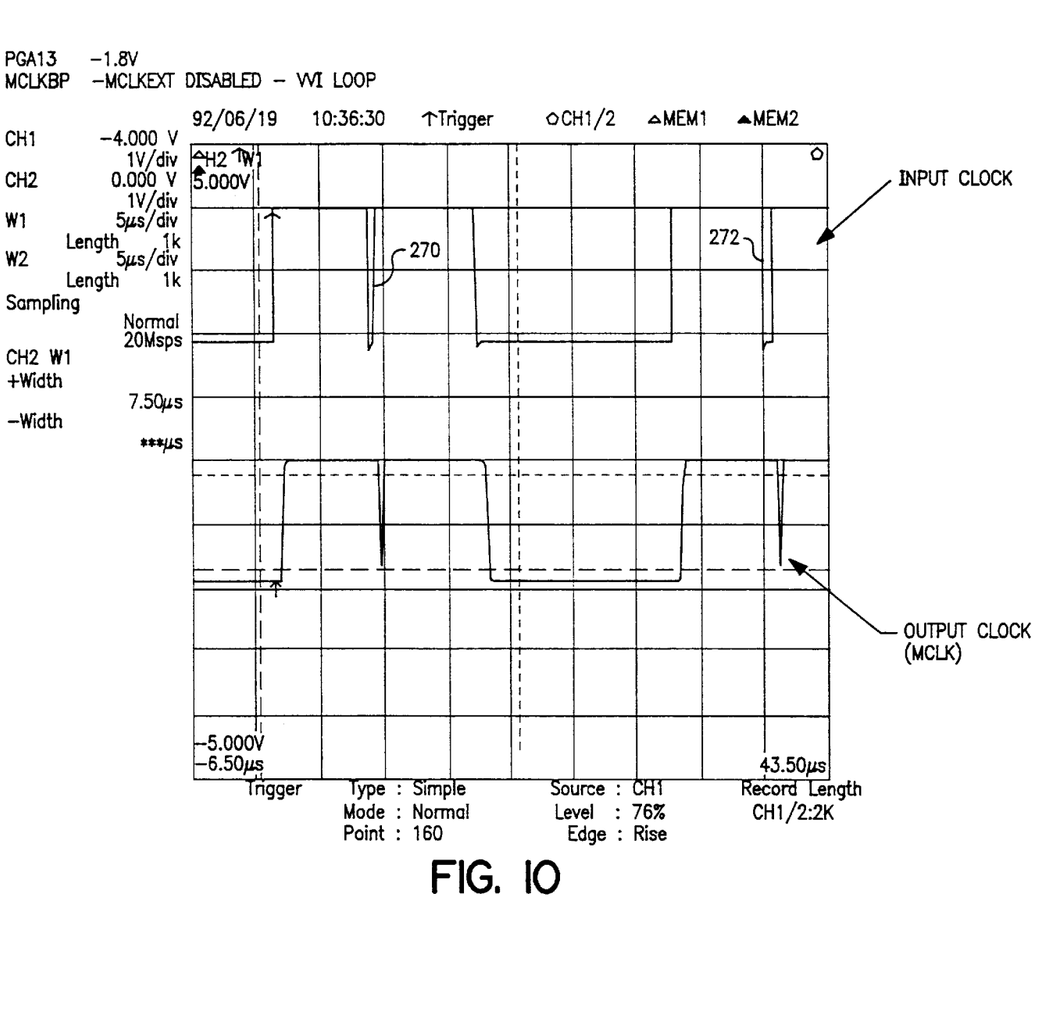
FIG. 10 is lab data from a functional device illustrating the inventive sub-block turned off resulting in a glitch on the original master clock propagating through the inventive sub-block and showing up on the modified master clock signal.

FIG. 10 exemplifies the susceptibility of prior art clocking systems to noise glitches. For example, noise glitches 270 and 272 propagate through input clock XTALOUT 210 and are eventually delivered to the implantable pulse generator (IPG) when sub-system 200 is turned off. This is the same situation presented by previously used IPG clock systems.

Figure 11:
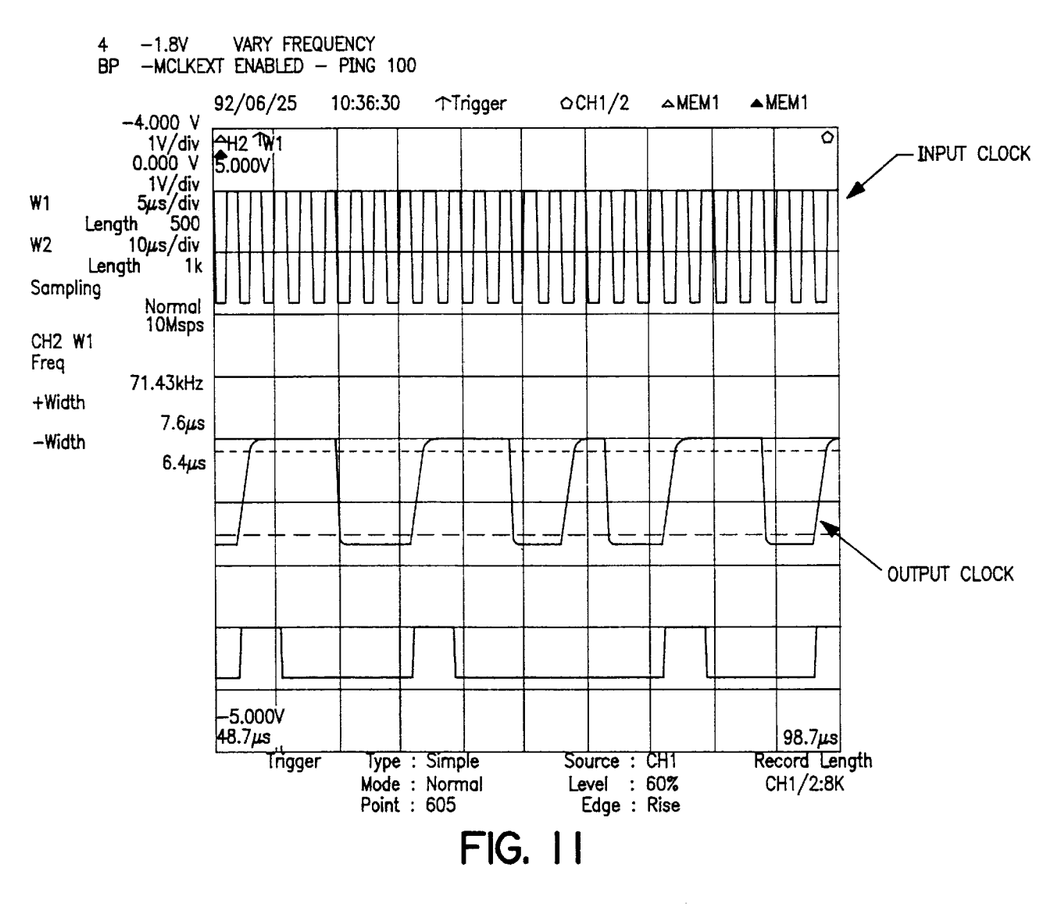
FIG. 11 is lab data from a functional device illustrating the ability of the inventive sub-block to run normally with an incoming master clock signal frequency set to 1 Mhz.

In FIG. 11, the ability of the preferred embodiment 200 to run at a 'natural frequency' with an input clock XTALOUT 210 frequency set at 1 MHz is illustrated with still more laboratory data from a functional device.

While the invention has been described above in connection with a particular embodiment, one skilled in the art will appreciate that the invention is not necessarily so limited. It will thus be understood that numerous other embodiments, examples, uses, modifications of, and departures from the teachings disclosed may be made, without departing from the scope of the present invention as claimed herein.

We claim:

1. A clock circuit for providing a main clock signal having periodic logic state transitions to an associated circuit which performs actions in response to said logic state transitions of said main clock signal and provides completion signals indicating completion of said actions performed in response to a preceding logic state transition of said main clock signal, wherein said clock circuit comprises:

a main clock output means for providing said main clock signal to said associated circuit;

a clock signal input means for receiving an input clock signal having periodic logic state transitions;

completion signal input means for receiving said completion signals from said associated circuit;

means responsive to occurrence of a logic state transition of said input clock signal for causing a logic state transition of said main clock signal, said responsive means further comprising logic means responsive to receipt of a said completion signal indicating completion of actions performed in response to a preceding logic state transition of said main clock signal, for delaying said transition of said logic state of said main clock signal until receipt of said completion signal.

2. A clock circuit as in claim 1, wherein said logic means further comprises first delay means for providing a delayed completion signal a first delay interval after receipt of a said completion signal and wherein said logic means comprises means for delaying a transition of said logic state of said main clock signal until occurrence of said delayed completion signal.

3. A clock circuit as in claim 1, wherein said completion signal input means comprises means for preventing receipt of a said completion signal until expiration of a second delay interval following an immediately preceding logic state transition of said main clock signal.

4. A clock circuit for providing a main clock signal having periodic logic state transitions to an associated circuit which performs actions in response to said logic state transitions of said main clock signal and provides a plurality of completion signals each indicating completion of actions performed in response to a preceding logic state transition of said main clock signal, said clock circuit comprising:

a main clock output means for providing said main clock signal to said associated circuit;

a clock signal input means for receiving an input clock signal having periodic logic state transitions;

completion signal input means for receiving said plurality of completion signals from said associated circuit;

means responsive to occurrence of a logic state transition of said input clock signal for causing a logic state transition of said main clock signal said responsive mans further comprising logic means responsive to receipt of a said completion signal indicating completion of actions performed in response to a preceding logic state transition of said main clock signal for delaying said transition of said logic state of said main clock signal until receipt of said plurality of completion signals.

5. A system comprising a clock circuit for providing a main clock signal having periodic logic state transitions and an associated circuit which performs actions in response to said logic state transitions of said main clock signal wherein said associated circuit comprises means for providing completion signals indicating completion of said actions performed in response to a preceding logic state transition of said main clock signal, and wherein said clock circuit comprises a main clock output means for providing said main clock signal to said associated circuit, a clock signal input means for receiving an input clock signal having periodic logic state transitions completion signal input means for receiving said completion signals from said associated circuit and means responsive to occurrence of a logic state transition of said input clock signal for causing a logic state transition of said main clock signal, said responsive means further comprising logic means responsive to receipt of a said completion signal indicating completion of actions performed in response to a preceding logic state transition of said main clock signal for delaying a said transition of said logic state of said main clock signal until receipt of a said completion signal.

6. A system as in claim 5, wherein said logic means further comprises first delay means for providing a delayed completion signal a first delay interval after receipt of a said completion signal and wherein said logic means comprises means for delaying said transition of said logic state of said main clock signal until occurrence of said delayed completion signal.

7. A system circuit as in claim 5, wherein said completion signal input means comprises means for preventing receipt of a said completion signal until expiration of a second delay interval following an immediately preceding logic state transition of said main clock signal.

8. A system comprising a clock circuit for providing a main clock signal having periodic logic state transitions and an associated circuit which performs actions in response to said logic state transitions of said main clock signal, wherein said associated circuit comprises means for providing a plurality of completion signals each indicating completion of actions performed in response to a preceding logic state transition of said main clock signal, and wherein said clock circuit comprises a main clock output means for providing said main clock signal to said associated circuit, a clock signal input means for receiving an input clock signal having periodic logic state transitions, completion signal input means for receiving said plurality of completion signals from said associated circuit and means responsive to occurrence of a logic state transition of said input clock signal for causing a logic state transition of said main clock signal, said responsive means further comprising logic means responsive to receipt of a said completion signal indicating completion of actions performed in response to a preceding logic state transition of said main clock signal for delaying a said transition of said logic state of said main clock signal until receipt of said plurality of completion signals.

\* \* \* \* \*